United States Patent [19]

Dolliver

[11] Patent Number: 4,895,162
[45] Date of Patent: Jan. 23, 1990

[54] APNEA MONITOR BELT

[76] Inventor: Marla Dolliver, 11416 W. 126th Ave., Cedar Lake, Ind. 46303

[21] Appl. No.: 244,927

[22] Filed: Sep. 15, 1988

[51] Int. Cl.⁴ .............................................. A61B 5/08
[52] U.S. Cl. ................................... 128/721; 128/802; 128/384
[58] Field of Search ............... 128/716, 721, 723, 782, 128/644, 384, 385, 904, 204.23, 203.14, 719, 387, 388, 389, 783, 802, 798, 791, 793; 2/338, 250

[56] References Cited

U.S. PATENT DOCUMENTS

| | | | |
|---|---|---|---|
| 226,658 | 4/1880 | Graydon | 2/338 |
| 448,128 | 3/1891 | Crisp et al. | 128/385 |
| 631,733 | 8/1899 | Bonfils et al. | 128/802 |
| 763,657 | 6/1904 | Brown | 128/802 |
| 4,381,012 | 4/1983 | Russek | 128/644 |

Primary Examiner—Max Hindenburg
Assistant Examiner—Scott Getzow
Attorney, Agent, or Firm—Allegretti & Witcoff, Ltd.

[57] ABSTRACT

An improved belt having two opposing sides, an electrode side and a lead side. The belt being capable of supporting reusable electrodes on its electrode side. The belt is further provided with a lead pocket at each end, and at least one vent intermittent the two lead pockets. A pair of monitor lead wires having been connected to the electrodes pass through the vent to the lead side of the belt and are inserted into the lead pockets through a lead hole. The belt is also provided with a means for clasping at its two ends, so the belt can be securely fitted on an infant.

10 Claims, 2 Drawing Sheets

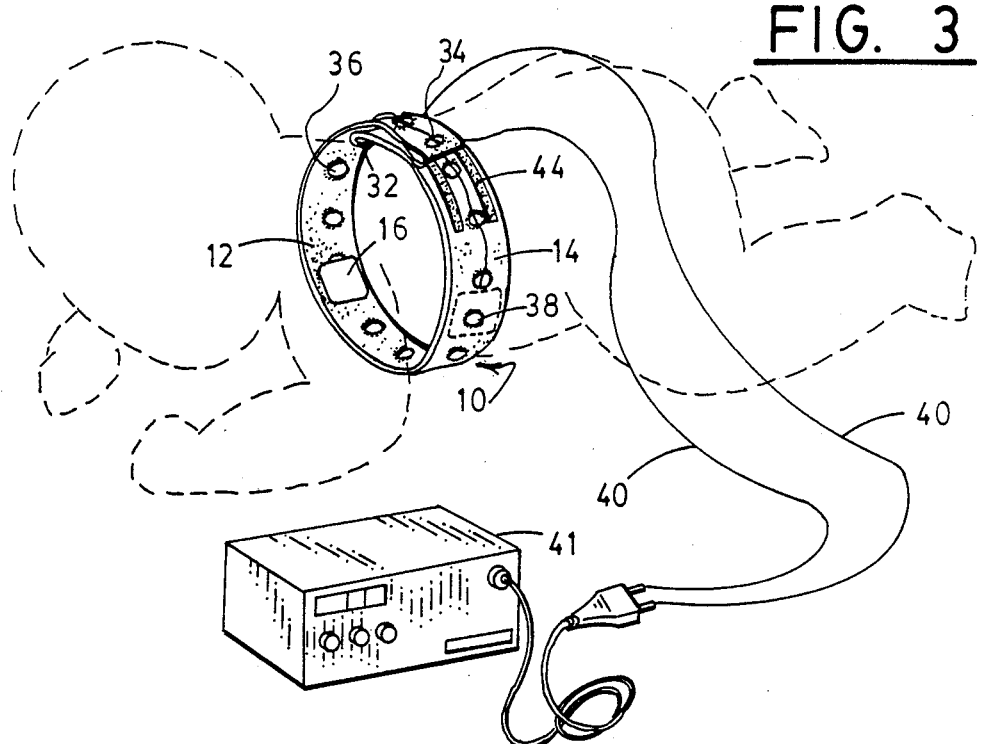
FIG. 3
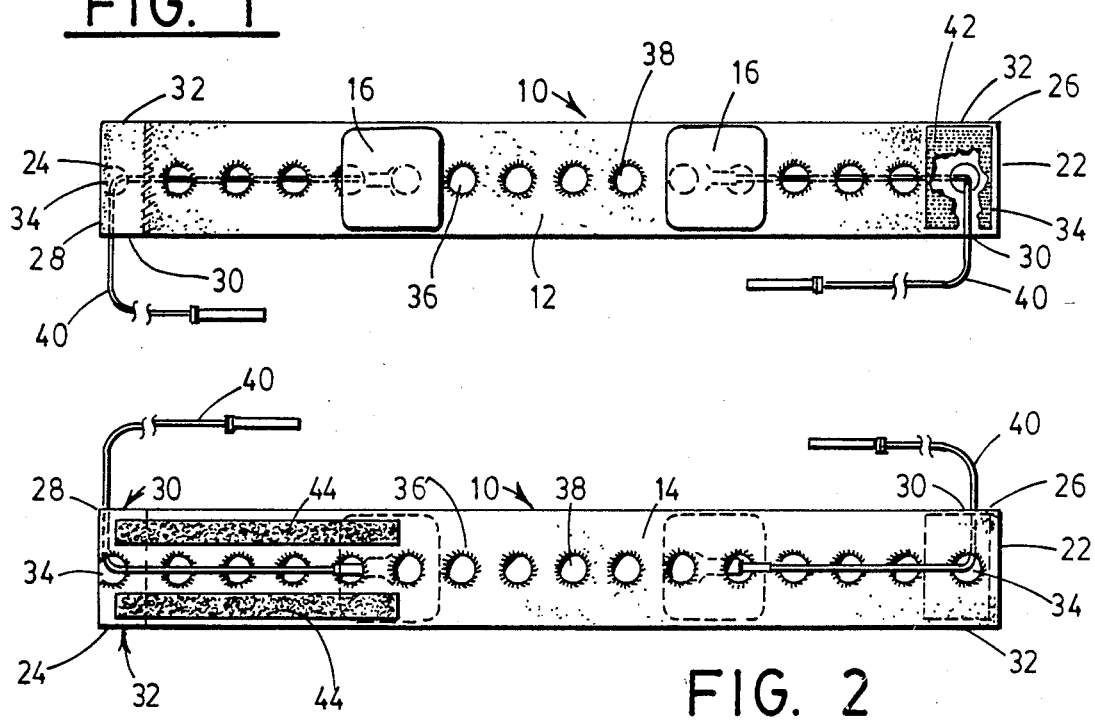
FIG. 1
FIG. 2

APNEA MONITOR BELT

BACKGROUND OF THE INVENTION

I. Field of the Invention

This invention relates to a device for securing electrodes against an infant's skin, to allow the monitoring of the infant's vital signs.

II. Description of the Prior Art

When a child is born prematurely it is important that its breathing and heart rate be monitored on an almost continuous basis. In order to do so electrodes, designed to detect the vital signs, must be put in contact with the infant. Monitor lead wires connect the electrodes to a monitor. The monitor records the breathing and heart activity of the infant, allowing early detection of any emergency situation.

In the prior art electrodes had been secured to an infant using two different methods. In the first of these methods, the electrode was actually glued to the infant's skin. This is obviously an undesirable method because of the irritation caused by the attachment and removal of such devices.

The second method used to secure electrodes has been an electrode belt. The prior art belts when wrapped around the infants, would hold the electrodes in contact with the infant. These prior art belts had several problems. The most significant of the problems was skin irritation. The design of the belts caused an infant to perspire which in turned irritated the skin and could cause a severe rash.

Another problem with the prior art belts was the infant's access to the monitor lead wires. Whenever an electrode loses contact with the infant or a monitor lead is disconnected from the electrode, the monitor will give a loose lead alarm. Such an alarm can be both distressing and inconvenient for a parent. The design of the prior art belts gave an infant direct access to the connection between the monitor leads and the electrodes. As such, an infant could, and often did, pull the lead from the electrode causing the alarm to sound. Moreover, because the belt would cause discomfort for the infants, i.e. perspiration and resulting rash, infants had a tendency to move the belt causing the electrode to lose contact with the skin, and resulting in the sounding of the alarm. Therefore, there remains a need for a device to secure monitor electrodes to an infant without causing the infant discomfort, and which inhibits the infant from causing the monitor leads to disconnect from the electrodes or the electrode to separate from the infant.

SUMMARY OF THE INVENTION

Briefly the invention relates to an improved apnea monitor electrode belt. The improved belt has two opposing sides, an electrode side and a lead side. The belt being capable of supporting reusable electrodes on its electrode side. The belt is further provided with a lead pocket at each end, and at least one vent intermittent the two lead pockets. A pair of monitor lead wires having been connected to the electrodes pass through the vent to the lead side of the belt and are inserted into the lead pockets through a lead hole. The belt is also provided with a means for clasping at its two ends, so the belt can be securely fitted on an infant.

The advantage of having vents in the belt are twofold. The vents allow air to get to an infant's skin under the belt, thereby significantly reducing, if not eliminating, the irritation of the skin. Additionally, the vents allow passage of the monitor lead wire through the belt, thereby removing the wire from direct reach of the infant.

The lead pockets further secure the lead wire and inhibit disconnection by the infant. Running the lead wires outside the belt and through the lead pockets makes the wires less accessible to the infant, and therefore less likely to be pulled away from the electrodes.

It is an object of this invention to provide an improved apnea monitor belt that minimizes the discomfort of the infant, and inhibits the infant from disconnecting the sensing electrodes.

It is another object of this invention to provide a apnea monitor belt that is reuseable and long lasting.

It's yet another object of this invention to provide a apnea monitor belt that allows an infant's vital signs to be monitored with minimal discomfort to the infant.

It is a further object of this invention to reduce the number of loose lead alarms caused by movement of the infant, which result in either a disconnection of the lead wires or the electrodes loosing contact with the infant.

These and other objectives and advantages will become apparent from the following detailed description of the preferred embodiments and claims.

BRIEF DESCRIPTION OF THE DRAWING

FIG. 1—A perspective view of the belt showing the electrodes attached.

FIG. 2—A perspective view of the opposing side of FIG. 1 showing the interaction of the belt and the lead wires.

FIG. 3—A depiction of the belt as it is secured to an infant.

DETAILED DESCRIPTION OF THE PREFERRED EMBODIMENT

Figure 4:
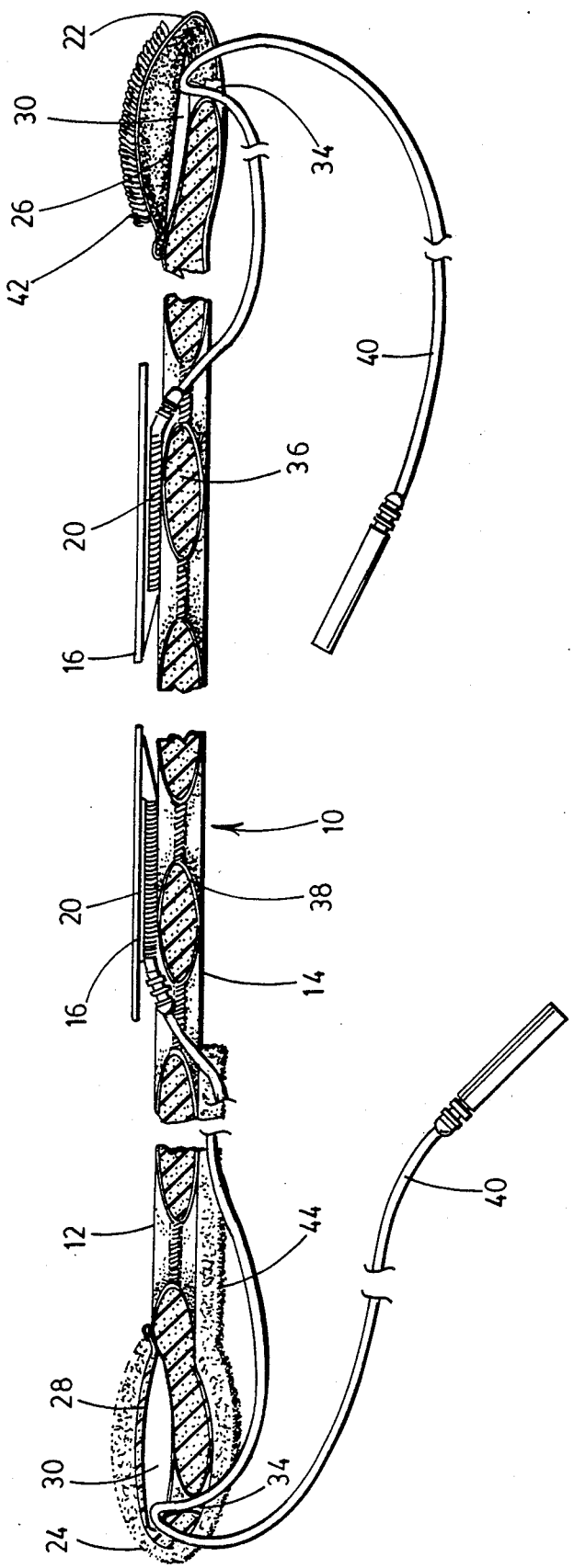
FIG. 4—A top view of the belt.

The preferred embodiment of the invention is shown in FIGS. 1 and 2. The belt 10 is of an appropriate length to wrap around the torso of a new born infant. Generally, 24 inches is deemed appropriate. The belt 10 may be constructed out of any appropriate material, however, because the skin of a new born infant is very sensitive, a soft and flexible material is preferred. Such a material is double looped faced polyurethane foam. The belt becomes even less irritating to an infant's skin if it is covered with infant flame retardant cloth.

The belt defines two opposing sides, an electrode side 12 and a lead side 14. A pair of electrodes 16, are operatively attached to the electrode side 12 of the belt 10. The electrodes 16 are reusable electrodes which can be found on the market. Any appropriate means may be used to attach the electrode to the belt. In a preferred embodiment, the electrode has a pair of Velcro™ pads 20 which allow easy and firm attachment to either the looped surface of the polyurethane foam, or to the surface of the infant flame retardant cloth.

The belt 10 further defines a first end 22 and a second end 24. A first lead pocket 26 and a second lead pocket 28 are located at the first and second ends 22, 24 respectively. Each lead pocket 26, 28 has an upper lead slot 30 at its upper end, and a lower lead slot 32 at its lower end. The lead pockets 26, 28 each define a lead hole 34 intermittent the upper lead slot 30 and the lower lead slot 32 on the lead side 14 of the belt 10. The lead hole 34 allows access to the interior of the lead pocket 26, 28 from the lead side 14 of the belt 10.

Intermittent the lead pockets 26, 28 there is a series of vents 36 which pierce the belt 10 allowing access from the electrode side 12 to the lead side 14. These vents 36 can be of any appropriate size, shape or number. In a preferred embodiment the vents 36 are round and cut into the belt 10 about one inch apart, center to center as shown in FIGS. 1 and 2. The edges 38 of the vents 36 should be smooth, so as to avoid any irritation of the infants skin. The vents 36 allow air to pass through the belt 10 to the skin of the infant. This will reduce any incidence of perspiration caused by the belt 10, and thereby reduce rashes that may result from said perspiration. The vents 36 also provide a means for passing a monitor lead wire 40 from the electrode side 12 of the belt 10 to the lead side 14 of the belt 10.

A pair of monitor lead wires 40 are operatively connected to the electrodes 16. The lead wires 40 then pass through the vent 36 nearest the electrode 16 so that they now hang on the lead side 14 of the belt 10 away from the infant's skin. The lead wires 40 then passed through the lead hole 34 of the lead pocket 26, 28, and out either the upper slot 30 or lower slot 32 of the lead pocket 26, 28. The positioning of the lead wires 38 in this way inhibits the ability of the infant to pull the wires 40 from either the monitor 41 or the electrodes 16.

Once the electrodes 16 and lead wires 40 are positioned as above described, the belt 10 is wrapped around the torso of an infant so that the electrodes 16 are in contact in the appropriate place to monitor breathing and/or heart rate. Positioning is shown in FIG. 4. The belt is secured by a clasping means. Any appropriate clasping means such as a snap, a button or a hook would suffice. However, because the belt 10 is intended to be reuseable, and because infants grow at a rapid rate, an adjustable clasping means is preferred. In a preferred embodiment, a self-adhesive cloth pad 42, such as Velcro TM is attached to the electrode side 12 of the belt 10 at the first lead pocket 26. This pad 42 is positioned to cooperate with a pair of self adhesive cloth strips 44, such as Velcro TM on the lead side 14 of the belt 10 extending from the second lead pocket 28 toward the first lead pocket 26. With this design the belt 10 is easily adjustable and can be securely fitted onto the infant. The secure fit coupled with the comfort supplied by the vents 36 and softer surface will inhibit the infant from altering the position of the belt 10 and, causing the electrode 16, 18 to lose contact with the infant's skin.

The preferred embodiment of the invention is now fully described. The above description is illustrative of the present invention, and is not intended to limit the invention in spirit or scope. Only the following claims and their equivalent limit the scope of the invention.

What I claim is:

1. An improved apnea monitor belt comprising, in combination:
    a belt, said belt having a first end and a second end and defining at least one vent intermittent the first end and the second end;
    a first lead pocket at said first end of said belt, said first lead pocket having an upper and a lower end and defining a lead slot at one of said upper and lower ends and further defining a lead hole intermittent said upper and lower ends, said lead hole allowing access to the interior of said first lead pocket;
    a second lead pocket, at said second end of said belt, said second lead pocket having upper and a lower ends and defining a lead slot at one of said upper and lower ends and further defining a lead hole intermittent said upper and lower ends, said lead hole allowing access to the interior of said second lead pocket; and
    means for clasping the first end of said belt to the second end of said belt, whereby the belt can be securely fastened around the torso of an infant.

2. The apnea monitor belt of claim 1 wherein said belt is made of double looped face polyurethane foam.

3. The apnea monitor belt of claim 1 further comprising a cover made of infant flame retardant cloth.

4. The apnea belt of claim 1 wherein the clasping means is adjustable.

5. The apnea belt of claim 1 wherein at least one vent comprises a series of round vents cut into said belt about one inch apart, center to center.

6. An improved apnea monitor belt comprising, in combination:
    a belt, said belt having a first end, a second end, an electrode side and a lead side and defining at least one vent intermittent the first end and the second end passing through the belt allowing access from said electrode side to said lead side;
    a first lead pocket at said first end of said belt, said first lead pocket having an upper and a lower end and defining a lead slot at one of said upper and lower ends and further defining a lead hole intermittent said upper and lower ends, said lead hole allowing access to the interior of said first lead pocket;
    a second lead pocket, at said second end of said belt, said second lead pocket having a upper and a lower end and defining a lead slot at one of said upper and lower ends and further defining a lead hole intermittent said upper and lower ends, said lead hole allowing access to the interior of said second lead pocket;
    a set of electrodes adapted to be secured to the electrode side of said belt near said vent;
    a set of monitor lead wires adapted to connect to said electrodes, each said lead wire passing through said vent to said lead side of said belt, traversing said lead side of said belt, and passing through one of said lead pockets by way of its said lead hole and said lead slot; and
    means for clasping the first end of said belt to the second end of said belt, whereby the belt can be securely fastened around the torso of an infant.

7. The apnea monitor belt of claim 6 wherein said belt is made of double looped face polyurethane foam.

8. The apnea monitor belt of claim 6 further comprising a cover made of infant flame retardant cloth.

9. The apnea belt of claim 6 wherein the clasping means is adjustable.

10. The apnea belt of claim 6 wherein at least one vent comprises a series of round vents cut into said belt about one inch apart, center to center.

* * * * *